United States Patent [19]

Breitzke et al.

[11] Patent Number: 5,362,479
[45] Date of Patent: Nov. 8, 1994

[54] ETHER SULFATES FOR ORAL HYGIENE AND DENTAL CARE PREPARATIONS

[75] Inventors: Willi Breitzke; Holger Tesmann, both of Duesseldorf; Karl-Heinz Gantke, Moenchengladbach; Hans-Christian Raths, Monheim, all of Germany

[73] Assignee: Henkel Kommanditgesellschaft auf Aktien, Duesseldorf-Holthausen, Germany

[21] Appl. No.: 90,072
[22] PCT Filed: Dec. 13, 1991
[86] PCT No.: PCT/EP91/02406
§ 371 Date: Jul. 19, 1993
§ 102(e) Date: Jul. 19, 1993
[87] PCT Pub. No.: WO92/12701
PCT Pub. Date: Aug. 6, 1992

[30] Foreign Application Priority Data

Jan. 19, 1991 [DE] Germany .............. 4101515

[51] Int. Cl.$^5$ .............................. A61K 7/16
[52] U.S. Cl. ........................ 424/49; 424/56; 252/174.17
[58] Field of Search .................... 424/49–55

[56] References Cited

U.S. PATENT DOCUMENTS

| | | | |
|---|---|---|---|
| 3,689,637 | 9/1972 | Pader | 424/52 |
| 3,939,262 | 2/1976 | Kim | 424/52 |
| 4,312,845 | 1/1982 | Wason | 423/339 |
| 4,483,780 | 11/1984 | Llenado | 252/135 |
| 4,732,696 | 3/1988 | Urfer | 252/174.17 |
| 4,748,158 | 5/1988 | Biermann et al. | 514/25 |
| 4,920,100 | 4/1990 | Lehmann et al. | 514/23 |
| 4,923,685 | 5/1990 | Wuelknitz et al. | 424/54 |
| 5,106,573 | 3/1992 | Bazzer | 252/174.17 |
| 5,109,127 | 4/1992 | Sekiguchi et al. | 536/115 |
| 5,145,665 | 9/1992 | Klueppel et al. | 424/50 |
| 5,200,328 | 4/1993 | Kirk et al. | 435/101 |

FOREIGN PATENT DOCUMENTS

| | | |
|---|---|---|
| 0006105 | 1/1980 | European Pat. Off. . |
| 0018463 | 11/1980 | European Pat. Off. . |
| 0020867 | 1/1981 | European Pat. Off. . |
| 0033359 | 8/1981 | European Pat. Off. . |
| 0046582 | 3/1982 | European Pat. Off. . |
| 0046947 | 3/1982 | European Pat. Off. . |
| 0082554 | 6/1983 | European Pat. Off. . |
| 0095562 | 12/1983 | European Pat. Off. . |
| 0190010 | 8/1986 | European Pat. Off. . |
| 0321053 | 6/1989 | European Pat. Off. . |
| 2203379 | 8/1972 | Germany . |
| 1373003 | 11/1974 | United Kingdom . |
| 9105764 | 5/1991 | WIPO . |

*Primary Examiner*—Shep K. Rose
*Attorney, Agent, or Firm*—Ernest G. Szoke; Wayne C. Jaeschke; Henry E. Millson, Jr.

[57] ABSTRACT

Oral hygiene and dental care compositions which contain an alkyl ether sulfate mixture corresponding to formula I $$R^1-O-(C_2H_4O)_x-SO_3M \qquad (I)$$

in which $R^1$ is a linear alkyl group containing 12 to 18 carbon atoms, M is an alkali metal or magnesium ion, and x has an average value of 2 to 10, and wherein at least 50% by weight of the mixture consists of homologs with $x-1$ to $x+1$ glycol ether groups, and the content of alkyl sulfates in which $x=0$ is below 10% by weight.

The invention also relates to dry powders containing the above alkyl ether sulfate mixture.

19 Claims, No Drawings

ETHER SULFATES FOR ORAL HYGIENE AND DENTAL CARE PREPARATIONS

This invention relates to the use of special alkyl ether sulfates as a surfactant component in oral hygiene and dental care preparations.

Oral hygiene and dental care preparations are used for cleaning the teeth and the oral cavity, for eliminating unwanted halitosis and for keeping the teeth and gums in a healthy state.

These effects are achieved through the cooperation of various components of which water, surfactants, flavorings and sweeteners and also abrasives and polishes are the most important. The function of the surfactants is to ensure thorough wetting of the oral cavity and the teeth, to facilitate the removal of plaque, to disperse or solubilize the flavorings and to generate foam to a certain extent, particularly in the case of toothpastes. They should not attack the oral mucosa, should have a neutral taste, should not affect the sense of taste and should not enter into any unwanted interactions with the other components of the oral hygiene and dental care preparations.

Soaps and alkyl sulfates have long played a dominant role as surfactants for toothpastes. Whereas soaps were largely displaced by alkyl sulfates on account of their high pH value and their low foaming power, alkyl sulfates have recently fallen into disrepute on account of the increased requirements which toothpaste surfactants are having to satisfy in regard to compatibility with mucous membrane.

Although alkyl ether sulfates, for example fatty alcohol polyglycol ether sulfates, have occasionally been proposed as surfactants for toothpastes and mouthwashes and although they are distinguished from alkyl sulfates by better solubility in water and compatibility with mucous membrane, they have never been adopted for use in practice because the industrially obtainable products have a bitter taste which is unacceptable in oral hygiene and dental care preparations.

It has now been found that alkyl ether sulfates having an average content of 2 to 10 glycol ether groups, which satisfy a limited specification in regard to homolog distribution and alkyl sulfate content, ideally fulfil the taste requirements which a surfactant for oral hygiene and dental care preparations is expected to satisfy.

The present invention relates to the use of alkyl ether sulfate mixtures corresponding to formula (I)

$$R^1\text{—}O\text{—}(C_2H_4O)_x\text{—}SO_3M$$

in which $R^1$ is a linear alkyl group containing 12 to 18 carbon atoms, M is an alkali metal or magnesium ion and x has an average value of 2 to 10, at least 50% by weight of the mixture consisting of homologs with $x-1$ to $x+1$ glycol ether groups and the content of alkyl sulfates in which $x=0$ being below 10% by weight, as a surfactant component in oral hygiene and dental care preparations.

Processes for the production of narrow-range ether sulfates such as these with their reduced alkyl sulfate content have recently been developed. The starting materials used are adducts of 2 to 10 mol ethylene oxide with linear fatty alcohols containing 12 to 18 carbon atoms which have been produced by any of the known ethoxylation processes that give narrow range ethoxylates. Ethoxylation processes such as these are described, for example, in EP-A-6 105, EP-A-18 463, EP-A-20 867, EP-A-33 359, EP-A-46 582, EP-A-46 947, EP-A-82 554, EP-A-95 562 or EP-A-321 053.

A particularly preferred ethoxylation process is described in EP-A-339 426. In this process, alkyl polyglycol ether mixtures suitable as starting products for ether sulfate production are obtained by addition of 2 to 10 mol and preferably 3 to 6 mol ethylene oxide onto 1 mol of a $C_{12-18}$ fatty alcohol in the presence of calcined hydrotalcites as catalysts. The alkyl polyglycol ethers are sulfated in known manner by reaction with chlorosulfonic acid or sulfur trioxide and neutralization of the sulfation product with aqueous alkali metal of magnesium hydroxide, preferably with aqueous sodium hydroxide.

The alkyl ether sulfates obtained in this way have a very low content of alkyl sulfate of less than 10% by weight, based on the anionic surfactant content. Certain amounts of unsulfated ethoxylate, usually of the order of 2 to 10% by weight of the anionic surfactant content, are present as secondary products in the end product.

The alkyl ether sulfate mixtures of formula I to be used in accordance with the invention show high foaming power under typical teeth cleaning conditions. Alkyl ether sulfate mixtures of formula I, in which $R^1$ is a linear $C_{12-14}$ alkyl group, M is a sodium ion and x has an average value of 3 to 6 and the content of alkyl sulfate with $x=0$ is below 5% by weight, foam particularly well in typical toothpaste compositions. The oral hygiene and dental care preparations produced with these alkyl ether sulfate mixtures also show very good compatibility with mucous membrane.

The present invention also relates to oral hygiene and dental care preparations containing surfactants, flavorings and sweeteners and, optionally, abrasives and polishes in an aqueous carrier which contain alkyl ether sulfate mixtures of formula I in a quantity of 0.1 to 5% by weight as surfactant component.

In the context of the invention, oral hygiene and dental care preparations are understood above all to be mouthwashes and toothpastes. The flavoring component present in such preparations is preferably peppermint oil, curly mint oil, anise oil, Japanese anise oil, caraway oil, eucalyptus oil, fennel oil, cinnamon oil, clove oil, geranium oil, sage oil, pimento oil, thyme oil, marjoram oil, basil oil, citrus oil, gaultheria oil or one or more components of these oils isolated therefrom or synthetically produced, such as for example menthol, carvone, anethol, cineol, eugenol, cinnamic aldehyde, caryophyllene, geraniol, citronellol, linalool, salvene, thymol, terpinene, terpineol, methyl chavicol and methyl salicylate. Other suitable flavorings are, for example, methyl acetate, vanillin, ionone, linalyl acetate, rhodinol and piperitone. Suitable sweeteners are either natural sugars, such as sucrose, maltose, lactose and fructose, or synthetic sweeteners, such as for example saccharin sodium, sodium cyclamate or aspartame.

In addition, mouthwashes according to the invention typically contain ethanol and astringent and toning drug extracts, dyes and preservatives or even antibacterial compounds.

Toothpastes according to the invention additionally contain humectants, such as for example sorbitol or glycerol, consistency regulators, deodorizing agents, substances active against oral and dental diseases, water-soluble fluorine compounds, such as sodium fluoride or sodium monofluorophosphate, and abrasives or polishes. Suitable abrasive and polishing components are, for example, chalk, dicalcium phosphate, insoluble sodium metaphosphate, aluminium silicate, calcium pyrophosphate, fine-particle synthetic resins, silicas, aluminium oxide, aluminium oxide trihydrate. These polishes preferably make up 15 to 50% by weight of the toothpaste.

It has now been found that particular advantages in terms of processing and application can be obtained by converting the alkyl ether sulfate mixtures to be used in accordance with the invention into free-flowing powders and incorporating them in this form in the oral hygiene and dental care preparations.

The aqueous solutions of the alkyl ether sulfate mixtures which accumulate in the production process cannot be converted into free-flowing powders simply by removal of water, for example by spray drying. Instead, the aqueous solutions or pastes have to be mixed with inert carrier materials and converted together with the carrier materials into the form of free-flowing powders by removal of water.

Suitable carriers are any chemically and physiologically inert inorganic carrier materials which are insoluble in water or show a substantially neutral reaction in water and which are particulate after drying. Particularly preferred carriers are substances which do not cause any problems when used in oral hygiene and dental care preparations, for example in toothpastes, for example because they are required to perform another function in preparations such as these. Suitable carriers such as these are, for example, the known polishing components, such as chalk, silicas, dicalcium phosphate, calcium pyrophosphate, insoluble sodium metaphosphate, aluminium oxide and aluminium oxide hydrates. However, neutral and physiologically acceptable water-soluble salts, such as for example sodium chloride or sodium sulfate or mixtures of two or more of these carriers, are also suitable. Other suitable inert carriers are alumosilicates, for example layer silicates, talcum, zeolites, magnesium aluminium silicate (Veegum®), calcium sulfate, magnesium carbonate or magnesium oxide.

Particularly preferred carriers are silicas which, by virtue of their large inner surface, give a particularly free-flowing preparation even in small quantities of about 0.5 part by weight per part by weight alkyl ether sulfate. In the case of other carriers, for example in the case of chalk and in the case of sodium chloride and sodium sulfate, the ratio by weight of carrier to alkyl ether sulfate should be at least 1:1 and better yet 1 to 10:1 in order to obtain applicationally favorable and sufficiently storable preparations.

Accordingly, the present invention also relates to a surfactant component for oral hygiene and dental care preparations consisting of surfactant and inert carriers, an alkyl ether sulfate mixture corresponding to formula I being present as surfactant in a quantity of 0.1 to 2 parts by weight per part by weight of the carrier. Silica in a quantity of 40 to 80% by weight is preferably present as carrier in the surfactant component.

The surfactant component according to the invention is produced by mixing an aqueous solution or paste of 1 part by weight of the alkyl ether sulfate mixture with 0.5 to 10 parts by weight of a suitable carrier, based on the ether sulfate content, preferably a fine-particle silica, and optionally water in such a quantity that a mixture still flowable at temperatures below $+80°$ C. is formed, and removing the water from this mixture by evaporation to such an extent that a particularly free-flowing powder is formed.

The removal of water from the mixture, i.e. drying of the paste or slurry, may be carried out in any way, for example on roller or belt dryers, in a fluidized bed of preformed preparation or by spraying into a hot air stream. The last of these processes, so-called spray drying, is the preferred method for drying the surfactant component according to the invention. The water is removed to such an extent that a particularly free-flowing powder is formed. In most cases, this is the case at water contents of less than 1% by weight. In cases where the carrier binds part of the water as water of crystallization, this recommended residual water content is based on the free water, i.e. the water which is not bound in the crystal lattice. In cases where relatively large agglomerates are formed during the drying process, for example where drying is carried out on roller and belt dryers, it may be necessary to disintegrate the agglomerates in a subsequent grinding process. Where the water is removed by spray drying, subsequent disintegration of the surfactant component according to the invention is not necessary. For use in toothpastes, the surfactant components according to the invention should not contain any agglomerates larger than $200\mu$ in diameter while the average primary particle size should not be more than $50\mu$.

In addition to the alkyl ether sulfate mixtures of formula I to be used in accordance with the invention, the oral hygiene and dental care preparations may also contain other neutral-tasting surfactants compatible with mucous membrane. A particularly suitable group of surfactants for this purpose are alkyl glycosides and alkyl oligoglucosides containing $C_{8-18}$ alkyl groups. Alkyl (oligo)glycosides such as these are obtained by reaction of sugars or starch with linear $C_{8-18}$ fatty alcohols or by reaction (transacetalization) of methyl or butyl glycosides with linear $C_{8-18}$ fatty alcohols.

A particularly suitable alkyl glucoside is an alkyl $(C_{12/14})$ oligo(1,4)glucoside having an average degree of oligomerization of 1.4 obtainable from lauryl and myristyl alcohol and glucose or starch. A surfactant component consisting of 10 to 50% by weight of an alkyl ether sulfate mixture corresponding to formula I, 10 to 50% by weight of an alkyl (oligo)glucoside and 40 to 80% by weight of a fine-particle silica which has been produced by spray drying shows particularly good taste and performance properties.

The powder-form surfactant components according to the invention are free-flowing and remain free flowing during storage, even in a humid atmosphere. Another advantage of the powder-form surfactant components obtainable by spray drying is that the content of free unsulfated fatty alcohol and the bitter taste are both further reduced by spray drying.

The following Examples are intended to illustrate the invention.

EXAMPLES

1. Production of alkyl ether sulfates suitable for use in accordance with the invention 1.1 Production of the starting ethoxylates To react commercial fatty alcohols with ethylene oxide, the particular alcohol was introduced into a pressure reactor and 0.5% by weight of the calcined hydrotalcite catalyst (catalyst A) described in EP 339 426 was added. The reactor was purged with nitrogen and evacuated for 30 minutes at a temperature of 100° C. The temperature was then increased to approx. 170° C. and the required quantity of ethylene oxide was introduced with stirring under a pressure of 4 to 5 bar. After the reaction and standing for another 30 minutes, products 1 to 5 characterized in Table I below were obtained following removal of the solid catalyst by filtration.

1.2 Production of the alkyl ether sulfates

Quantities of 1 mol of the ethers prepared in Examples 1 to 5 were introduced into a 1 liter sulfonation reactor with jacket cooling and reacted with 76 g (0.95 mol) gaseous sulfur trioxide at 30° C. to 45° C. The sulfur trioxide was driven out by heating from a corresponding quantity of 65% oleum, diluted with nitrogen to a concentration of 5% by volume and introduced into the fatty alkyl polyglycol ether over a period of 35 minutes. After the sulfation, the acidic reaction mixtures were stirred in portions into cold aqueous 25% sodium hydroxide, the temperature rising to approx. 35° C. under the effect of the heat of neutralization released, and adjusted to pH 7.

The anionic surfactant content (WAS) and the unsulfonated components (US) were determined in accordance with DGF-Einheitsmethoden, Stuttgart 1950–1984, H-III-10 and G-III-6b. The results are shown in Table II.

TABLE I

| | Product | | | | |
|---|---|---|---|---|---|
| | 1 | 2 | 3 | 4 | 5 |
| Starting alcohol | | | | | |
| Lauryl alcohol | 70% by weight | 50% by weight | 50% by weight | 50% by weight | 70% by weight |
| Myristyl alcohol | 30% by weight | 50% by weight | 50% by weight | 50% by weight | 30% by weight |
| Ethylene oxide added (mol/mol alcohol) | 2 | 3.6 | 4 | 5 | 7 |
| Homolog distribution (% by weight) | | | | | |
| $x = 0$ | 9 | 4.5 | 2.5 | 0.5 | Below 1 |
| 1 | 10.5 | 6 | 4 | 1 | Below 1 |
| 2 | 21 | 13 | 11 | 3 | Below 1 |
| 3 | 26 | 22.5 | 20.5 | 10.5 | 1.5 |
| 4 | 19 | 25 | 26.5 | 21.5 | 4 |
| 5 | 9.5 | 17 | 19.5 | 27.5 | 11 |
| 6 | 2.5 | 8 | 10 | 20.5 | 18.5 |
| 7 | 1 | 3 | 3.5 | 10.5 | 23 |
| 8 | Below 1 | 1.5 | 1.5 | 3.5 | 20 |
| 9 | | 0.5 | 1 | 1 | 12 |
| 10 | | Below 0.5 | Below 1 | 0.5 | 5 |
| 11 | | | | Below 0.5 | 2.5 |
| 12 | | | | | 1 |
| 13 | | | | | 1 |
| 14 | | | | | Below 1 |

TABLE II

| | Product | | | | |
|---|---|---|---|---|---|
| | 1 | 2 | 3 | 4 | 5 |
| WAS | 68.8 | 26.0 | 25.5 | 27.1 | 25.8 |
| US | 4.4 | 2.3 | 2.5 | 3.5 | 2.9 |

Products 1 to 5 were converted into powder form by various methods. Products 6 to 10 were obtained as follows:

Product 6

Spray drying of a mixture of product 1 and ground silica gel (Syloblanc ® 34, GRACE) to form a powder containing approx. 47.5% by weight WAS, 2.5% by weight US and 50% by weight SiO$_2$.

Product 7

Spray drying of a mixture of product 2 and ground silica gel (Syloblanc ® 34) to form a powder containing approx. 74% by weight WAS, 1% by weight US and 25% by weight SiO$_2$.

Product 8

Spray drying of a mixture of product 3 and ground silica gel (Syloblanc ® 34) to form a powder containing approx. 64.5% by weight WAS, 1.5% by weight US and 34% by weight SiO$_2$.

Product 9

Spray drying of a mixture of product 4 and ground silica gel (Syloblanc ® 34) to form a powder containing approx. 47.4% by weight WAS, 2.6% by weight US and 50% by weight SiO$_2$.

Product 10

Spray drying of a mixture of product 1, alkyl C$_{12/14}$ oligo(1,4)glucoside (APG) and ground silica gel (Syloblanc ® 34) to form a powder containing approx. 25% by weight product 1 (WAS+US), 25% by weight APG and 50% by weight SiO$_2$.

Product 11

Spray drying of a mixture of product 2, alkyl C$_{12/14}$ oligo(1,4)glucoside (APG) and ground silica gel (Syloblanc ® 34) to form a powder containing approx. 25% by weight product 2 (WAS+US), 25% by weight APG and 50% by weight SiO$_2$.

2. Performance tests

Products 1 to 10 were incorporated as "surfactant" in the following toothpaste formulation in such a quantity that 2% by weight surfactant (ether sulfate or ether sulfate/alkyl oligoglucoside mixture) was always present:

| | |
|---|---|
| Precipitated silica (Sident ® 12 DS) | 21.0 g |
| Thickening silica gel (Syloblanc ® 34) | 1.0 g |
| Sodium carboxymethyl cellulose | 1.2 g |
| Saccharin Na | 0.1 g |
| Na benzoate | 0.1 g |
| Oral hygiene flavoring oil 1/074568 (DRAGOCO) (peppermint flavor) | 1.0 g |
| Sorbitol (70% in H$_2$O) | 15.0 g |
| Glycerol (86% in H$_2$O) | 25.0 g |
| Sodium fluoride | 0.22 g |
| Surfactant (100%) | 2.0 g |
| Water | ad 100 g |

The toothpastes 2.1 to 2.10 obtained were tested by the rubbing foam test for their foaming power (20° C., 10 g/l, tapwater 10° Gh) and for taste under teeth cleaning conditions.

The toothpaste test formulation was produced for comparison using a normal broad-range alkyl ether sulfate (product 1 C) present in the form of an aqueous paste containing 71% by weight WAS and 2.1% by weight US.

Product 1 C: lauryl/myristyl (70:30) poly(2 EO)glycol ether sulfate, Na salt homolog distribution (% by weight)

$x=0$: 26% by wt $x=4$: 9% by wt $x=8$: 2% by wt
$x=1$: 18% by wt $x=5$: 6% by wt $x=9$: 2% by wt
$x=2$: 15% by wt $x=6$: 5% by wt $x=10$: 1% by wt
$x=3$: 12% by wt $x=7$: 4% by wt $x=11$: below 1% by wt.

1. Rubbing foam test

The test described in Fette, Seifen, Antstrichmittel 66 (1964), pages 955 to 961 was carried out with the EH-MEDA rubbing foam tester. To this end, 20 g toothpaste were dispersed in 180 g water and heated to 45° C. in the foam cylinder. Foam was then produced by rubbing for 60 seconds with a Perlon brush vertically rotating at 2600 r.p.m. against a cylindrical metal wire gauze. Table III below shows the foam volume 0.5 min. and 5 mins. after foam generation and the drainage water separated from the foam after 5 mins.

2. Taste evaluation

Taste evaluation was carried out after teeth cleaning by 5 independent test subjects on the basis of following criteria:

3 = flavor predominant, no foreign taste
2 = slight foreign taste
1 = strong foreign taste
AT = aftertaste For each test product, an average value was formed from the evaluations of the five test subjects. The results are set out in Table III.

TABLE III

| Test tooth-paste | Rubbing foam | | Drainage water | Taste |
|---|---|---|---|---|
| | After 0.5 min. | After 5 mins. | | |
| 2.1 | 1030 ml | 910 ml | 60 ml | 2 AT |
| 2.2 | 850 | 730 | 60 | 1 AT |
| 2.3 | 820 | 720 | 50 | 1 AT |
| 2.4 | 820 | 720 | 60 | 1 AT |
| 2.5 | 830 | 750 | 60 | 2 AT |
| 2.6 | 1040 | 920 | 70 | 2 AT |
| 2.7 | 850 | 740 | 60 | 2 AT |
| 2.8 | 900 | 780 | 60 | 2 AT |
| 2.9 | 830 | 720 | 60 | 2 AT |
| 2.10 | 1000 | 890 | 60 | 3 — |
| 2.11 | 800 | 700 | 50 | 3 — |
| 2.1 C | 1050 | 940 | 50 | 2 AT |

We claim:

1. In an oral hygiene or dental care composition comprising at least one surfactant, flavoring, and sweetener, the improvement wherein the composition contains a surfactant effective quantity of an alkyl ether sulfate mixture corresponding to formula I $$R^1-O-(C_2H_4O)_x-SO_3M \qquad (I)$$

in which $R^1$ is a linear alkyl group containing 12 to 18 carbon atoms, M is an alkali metal or magnesium ion, and x has an average value of 2 to 10, and wherein at least 50% by weight of the mixture consists of homologs with $x-1$ to $x+1$ glycol ether groups, and the content of alkyl sulfates in which $x=0$ is below 10% by weight; and wherein the composition is free from any additional quantities of alkyl sulfates.

2. The composition of claim 1 wherein in formula I $R^1$ is a linear alkyl group containing 12 to 14 carbon atoms, M is a sodium ion, x has an average value of 3 to 6 and the content of alkyl sulfate with $x=0$ is below 5% by weight.

3. The composition of claim 1 wherein the surfactant effective quantity of alkyl ether sulfate mixture is from 0.1 to 5% by weight.

4. The composition of claim 1 wherein the composition is a mouthwash.

5. The composition of claim 1 wherein the composition is a toothpaste.

6. The composition of claim 1 wherein the composition also contains at least one other neutral-tasting surfactant compatible with mucous membrane.

7. The composition of claim 1 wherein the composition also contains a $C_8-C_{18}$ alkyl glycoside, a $C_8-C_{18}$ alkyl oligoglucoside, or a mixture thereof as the at least one other surfactant.

8. The composition of claim 7 wherein the alkyl glucoside is an alkyl ($C_{12/14}$) oligo (1,4) glucoside.

9. The composition of claim 6 wherein the surfactant component of the composition is a spray dried powder consisting essentially of from 10 to 50% by weight of the alkyl ether sulfate mixture of formula I, from 10 to 50% by weight of a $C_8-C_{18}$ alkyl oligoglucoside, and from 40 to 80% by weight of a fine-particle silica.

10. The composition of claim 9 wherein the alkyl oligoglucoside is an alkyl ($C_{12/14}$) oligo (1,4) glucoside.

11. The composition of claim 10 wherein in the alkyl ether sulfate mixture of formula I $R^1$ is a linear alkyl group containing 12 to 14 carbon atoms, M is a sodium ion, x has an average value of 3 to 6 and the content of alkyl sulfate with $x=0$ is below 5% by weight.

12. A surfactant component for oral hygiene and dental care preparations in the form of a free-flowing powder consisting essentially of A) an alkyl ether sulfate mixture corresponding to formula I $$R^1-O-(C_2H_4O)_x-SO_3M \qquad (I)$$

in which $R^1$ is a linear alkyl group containing 12 to 18 carbon atoms, M is an alkali metal or magnesium ion, and x has an average value of 2 to 10, and wherein at least 50% by weight of the mixture consists of homologs with $x-1$ to $x+1$ glycol ether groups, and the content of alkyl sulfates in which $x=0$ is below 10% by weight, wherein said surfactant component is free from any additional quantities of alkyl sulfates; and B) a carrier material; wherein component A is present in from 0.1 to 2 parts by weight per part of component B.

13. The surfactant component of claim 12 wherein in formula I $R^1$ is a linear alkyl group containing 12 to 14 carbon atoms, M is a sodium ion, x has an average value of 3 to 6 and the content of alkyl sulfate with $x=0$ is below 5% by weight.

14. The surfactant component of claim 12 wherein component B is a fine-particle silica.

15. The surfactant component of claim 12 wherein the free-flowing powder is a spray dried powder.

16. The surfactant component of claim 12 which also contains a $C_8-C_{18}$ alkyl glycoside, a $C_8-C_{18}$ alkyl oligoglucoside, or a mixture thereof.

17. The surfactant component of claim 16 wherein the alkyl glucoside is an alkyl ($C_{2/14}$) oligo (1,4) glucoside.

18. The surfactant component of claim 16 wherein the free-flowing powder is a spray dried powder consisting of from 10 to 50% by weight of the alkyl ether sulfate mixture of formula I, from 10 to 50% by weight of a $C_8-C_{18}$ alkyl oligoglucoside, and from 40 to 80% by weight of a fine-particle silica.

19. The surfactant component of claim 18 wherein the alkyl oligoglucoside is an alkyl ($C_{12/14}$) oligo (1,4) glucoside.

* * * * *